(12) United States Patent
Giles-Komar et al.

(10) Patent No.: US 8,216,842 B2
(45) Date of Patent: Jul. 10, 2012

(54) ENHANCEMENT OF HYBRIDOMA FUSION EFFICIENCIES THROUGH CELL SYNCHRONIZATION

(75) Inventors: Jill Giles-Komar, Downington, PA (US); Michael Rycyzyn, Berwyn, PA (US); Gregory Bannish, Morton, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 178 days.

(21) Appl. No.: 12/443,492

(22) PCT Filed: Oct. 12, 2007

(86) PCT No.: PCT/US2007/081187
§ 371 (c)(1),
(2), (4) Date: Mar. 30, 2009

(87) PCT Pub. No.: WO2008/046033
PCT Pub. Date: Apr. 17, 2008

(65) Prior Publication Data
US 2010/0029002 A1 Feb. 4, 2010

Related U.S. Application Data

(60) Provisional application No. 60/829,347, filed on Oct. 13, 2006.

(51) Int. Cl.
*C12N 15/06* (2006.01)
*C12N 5/078* (2010.01)
*C12N 5/0781* (2010.01)
*C12N 5/16* (2006.01)
*C12N 5/20* (2006.01)

(52) U.S. Cl. .......... 435/449; 435/376; 435/452
(58) Field of Classification Search .......... 435/449
See application file for complete search history.

(56) References Cited

U.S. PATENT DOCUMENTS
5,989,907 A * 11/1999 Boyan et al. .......... 435/325
2004/0053832 A1 * 3/2004 Leskovar .......... 514/12

FOREIGN PATENT DOCUMENTS
JP 59051791 3/1984
JP 1-202295 * 8/1989

OTHER PUBLICATIONS

Abraham et al (European journal of Biochemistry, 1976, vol. 65, pp. 79-86).*
Byars and Kidson, (Nature, 1970, vol. 226, pp. 648-650).*
Sburlati et al (PNAS, 1991, vol. 88, p. 253-257).*
Lerner and Hodge (Journal of Cellular Physiology, 1971, vol. 77, pp. 265-276).*
Melchers and Lernhardt (PNAS, 1985, vol. 82, pp. 7681-7685).*
Krek and DeCaprio (Methods in Enzymology, 1995, vol. 254, pp. 114-124).*
abstract of Jp 1202295, 1989.*
Kohler et al., Nature, vol. 256, pp. 495-497 (1975).
Gefter et al., Somatic Cell Genetics, vol. 3, No. 2, pp. 231-236 (1977).
Goding, James, Monoclonal Antibodies: Principles and Practice, $2^{nd}$ Edition, Academic Press, pp. 59-103 (1986).
Goding James, Monoclonal Antibodies: Principles and Practice, $2^{nd}$ Edition, Academic Press, pp. 71-74, (1986).
International Search Report for PCT/US2007/081187 dated Jul. 4, 2007.
Miyahara et al., "Colcemid Treatment of Myeloma Prior to Cell fusion Increases the Yield of Hybridomas Between Myelom and Splenocyte", Biochemical and Biophysical Research Communications, vol. 124, No. 3, pp. 903-908 XP009101586.
Kues et al., "Cell Cycle Synchronization of Porcine Fetal Fibroplast: Effects of Serum Deprivation and Reversible Cell Cycle Inhibitors", Biology of Reproduction, Society for the Study of Reproductions, Champaign, IL, vol. 62, No. 2 pp. 412-419 (Jan. 1, 2000) XP000920566.
Yabe et al., "Enhanced formation of mouse hybridomas without hat treatment in a serum-free medium", In Vitro Cellular and Developmental Biology, The Association, Gaithersburg, MD, vol. 22, No. 7, pp. 363-368 (Jul. 1, 1986) XP009101527.
Kudo et al., "A Great Improvement of Fusion Efficiency in Mouse B Cell Hybridoma Production by Use of the New Culture Medium Git", Tohoku Journal of Experimental Medicine, vol. 153, No. 1, pp. 55-66 (1987) XP002484370.
Stadler et al., "Cell Cycle Changes and the Ability of Cells to Undergo Virus Induced Fusion", Proceedings of the Ntional Academy of Sciences of the United States of America, vol. 69, No. 7, pp. 1929-1933 (1972) XP002484371.
Kawamoto et al., "Development of a Serum-Free Medium for Growth of NS-1 Mouse Myeloma Cells and Its Application to the Isolation of NS-1 Hybridomas", Analytical Biochemistry, vol. 130, No. 2, pp. 445-453, (1983) XP009101589.

* cited by examiner

*Primary Examiner* — Karen A Canella
(74) *Attorney, Agent, or Firm* — Brian C. Carey

(57) ABSTRACT

The present invention provides methods of enhancing hybridoma fusion efficiencies through cell synchronization of the fusion partners, in order to aid in production of antibodies.

3 Claims, No Drawings

ENHANCEMENT OF HYBRIDOMA FUSION EFFICIENCIES THROUGH CELL SYNCHRONIZATION

CROSS-REFERENCE TO RELATED APPLICATIONS

This application claims the benefit of International Application Number PCT/US2007/081187, filed 12 Oct. 2007, which claims the benefit of U.S. Provisional Application No. 60/829,347, filed 13 Oct. 2006. The entire contents of each of the aforesaid applications are incorporated herein by reference in their entirety.

BACKGROUND OF THE INVENTION

1. Field of the Invention

The present invention relates to methods of enhancing hybridoma fusion efficiencies through cell synchronization of the fusion partners, in order to aid in production of antibodies.

2. Related Art

The use of monoclonal antibodies (mAbs) as therapeutic reagent has become an effective approach for the treatment of various diseases. In addition, mAbs are powerful tools to gain a better understanding of the immuno-pathogenesis of various diseases.

Generation of monoclonal antibodies has first been described by Kohler and Milstein (Kohler and Milstein, Nature 256: 495-497 (1975)) using the hybridoma technology and since then has become a standard procedure in the lab. A typical protocol for hybridoma generation involves: (i) immunizing an animal (e.g., mouse, rat or rabbit) with a purified protein antigen; (ii) harvesting antibody producing B-cells, typically from the spleen; (iii) fusing B-cells with a non-secretory myeloma cell line deficient for the enzyme hypoxanthine guanine phosphoribosyl transferase (e.g., x63-Ag 8. 653 from a BALB/c mouse strain); (iv) growing hybridoma cells in a selection medium containing hypoxanthine, aminopterin and thymidine (HAT) and (v) screening for cells that produce the desired antibody and (vi) limit dilution cloning to obtain a homogenous cell line that secretes the antibody.

In this time consuming multi-step process, one of the most critical steps is cell fusion, where antibody-secreting B cells and myeloma cells are fused. The murine HGPRT negative B cell myeloma cell line, FO, with a doubling time of 8-12 hours, has become a standard fusion partner in the hybridoma process. When fused to splenocytes from a mouse that is mounting a strong humoral immune response, FO-derived hybridomas that secrete the mAb of interest can be generated quickly.

However, the cell fusion process is very inefficient. Even under best known conditions, such as purity of reagents, temperature, and cell viability, only approximately 0.08% splenic antibody secreting cells are fused. Such inefficiency is due to many factors. For example, fusion of two splenic cells creates a hybridoma that is not immortalized and will not grow, and fusion of two myeloma cells creates a hybridoma that does not secrete antibody and will die under selection media. In addition, fusion of greater than two cells results in unstable syncytias and the polykaryons will not survive.

As a result of all these variables, initial hybridomas are often unstable and do not survive the selection process while the ones that do usually secrete low levels of antibody. Therefore, there is a need for improved methods to generate hybridomas and make monoclonal antibodies.

SUMMARY OF THE INVENTION

The present invention provides a method to increase hybridoma fusion efficiency, comprising synchronizing fusion partner cells. In one aspect, the present invention provides synchronization of antibody-producing B cells. In another aspect, the present invention provides synchronization of mouse myeloma cells.

In one embodiment, the synchronization is achievement through serum starvation. The method of the present invention provides a more efficient way of generating antibodies. Accordingly, in another aspect, the present invention provides antibodies produced using the improved method of the present invention. The antibodies produced using the present invention can be used for therapeutic, diagnostic, and/or research purposes.

DESCRIPTION OF THE INVENTION

Citations: All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2006); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2006); Colligan et al., Current Protocols in Protein Science, John Wiley & Sons, NY, N.Y., (1997-2006).

The term "immunogen" as used herein means any molecule that can potentially elicit an immune response in a subject. Since some immunogens do not elicit an immune response when administered in the absence of an adjuvant, the term "immunogen" encompasses molecules that only elicit an immune response when co-administered with an adjuvant.

The term "monoclonal antibody" as used herein refers to a preparation of antibody molecules of single molecular composition. A monoclonal antibody displays a single binding specificity and affinity for a particular epitope. Monoclonal antibodies include murine, human, humanized and chimeric monoclonal antibodies.

In general, antibodies are proteins or polypeptides that exhibit binding specificity to a specific immunogen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4.

In general, means for preparing and characterizing antibodies are well known in the art (e.g., Ausubel, Harlow and Lane, and Colligan, supra). An immunogen is administered according to the immunization schedule for the immunogen. For example, a single administration of the immunogen in an amount sufficient to elicit an effective immune response may be used. Alternatively, other regimes of initial administration of the immunogen followed by one or more boosting may be used. The administration may be via any suitable route, such as intraperitoneal, intravenous, subcutaneous, intramuscular, intradermal, or through footpad injection. Typically, rodents such as mice and rats may be used.

Following immunization, somatic cells with the potential for producing antibodies, specifically B lymphocytes (B cells), are selected for use in the mAb generating protocol. These cells may be obtained from spleens, tonsils or lymph nodes, or from a peripheral blood sample. The antibody-producing B cells from the immunized animal are then fused with cells of an immortal myeloma cell line. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul.

Methods for generating hybrids of antibody-producing spleen or lymph node cells and myeloma cells are well known in the art. Generally, somatic cells are mixed with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al. (1977). The use of electrically induced fusion methods is also appropriate (Goding pp. 71-74, 1986).

However, although all cells types are able to fuse, not all do so equally or with the ability to survive. For example, blastoid B cells, which are actively dividing, are the best cells to use for fusions with myeloma cells. If the B cell is not in the blastoid stage, its nucleus does not enter mitotic division at the same time as the nucleus of the myeloma cell and cell fusion will not occur. Also, too much antibody translation in the endoplasmic reticulum induces an unfolded protein response (UPR) that can inhibit translation and induce apoptosis. In other words, secretion of high amounts of antibody can occur only in cells optimized for protein secretion. Thus, cell cycle synchronization is a major contributor to hybridoma fusion efficiency, with the correct fusion between a B lymphoblast and an actively dividing myeloma cell—and only one of each.

The present invention provides an improved method for producing antibodies in which the standard methods can be manipulated to increase the efficiency of the fusion between the antibody-producing B cells and myeloma cells. In one embodiment, the myeloma cells are synchronized prior to the fusion with the antibody-producing B cells. In another embodiment, the antibody-producing B cells are synchronized prior to the fusion with the myeloma cells.

There are four main stages in the division cycle of mammalian cells. The G0/G1 period refers to the time between the end of telophase and start of DNA synthesis; the S period corresponds to the time taken by a cell to double its DNA content; the G2 period is the time between the end of DNA synthesis and beginning of prophase; and the M phase refers to mitosis. In order to synchronize a population of cells, there are several methods that can reversibly block cells at certain stages of the cell cycle. For example, nocodazole is an antimitotic agent that disrupts microtubules by binding to β tubulin and preventing formation of one of the two interchain disulfide linkages, thus inhibiting microtubule dynamics, disruption of mitotic spindle function, and fragmentation of the Golgi complex. Nocodazole arrests the cell cycle at G2/M phase. Other examples include mimosine, which is a plant amino acid and iron chelator that inhibits DNA replication and blocks the cell cycle in the G1/S phase; and aphidocolin, which prevents mitotic cell division by interfering with the activity of DNA polymerase, also blocking the cell cycle in the G1/S phase. In addition, growth of cells in media lacking serum induces cell cycle arrest at G1 in most cell types.

A large portion of exponentially growing cells in culture is in the G1 stage of the cell cycle. However, this stage may not be optimal for cell fusion. It has been found that following treatment of myeloma cells with colcemid, a mitotic spindle inhibitor that arrests cells at the metaphase stage of mitosis, there is an increase of 26-570% for colonies in hybridoma cell fusion. According to the present invention, cells can be grown in a synchronized manner using one or more cell cycle inhibitors followed by washing and/or restoration of normal growth media. In addition, by varying the amount of recovery time, the stage of the cell cycle in which the B cells or myeloma cells are in prior to fusion can be selected.

After the fusion, the population of hybridomas are cultured in selection media and specific hybridomas are selected. Typically, selection of hybridomas is performed by culturing the cells by single-clone dilution in microtiter plates, followed by testing the individual clonal supernatants (after about two to three weeks) for the desired reactivity. The assay may be radioimmunoassays, enzyme immunoassays, cytotoxicity assays, plaque assays, dot immunobinding assays, and the like.

Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA). Other suitable methods of producing or isolating antibodies of the requisite specificity can be used as known in the art, e.g., see, Colligan, Harlow and Lane, Ausubel, supra, each of which is entirely incorporated herein by reference. Methods for engineering or humanizing non-human or human antibodies can also be used and are well known in the art. Generally, a humanized or engineered antibody has one or more amino acid residues from a source which is non-human, e.g., but not limited to, mouse, rat, rabbit, non-human primate or other mammal. These human amino acid residues are often referred to as "import" residues, which are typically taken from an "import" variable, constant or other domain of a known human sequence. Known human Ig sequences are well known in the art and can any known sequence. See, e.g., but not limited to, Kabat et al., Sequences of Proteins of Immunological Interest, U.S. Dept. Health (1983) and PCT publication WO 05/33029 and U.S. Ser. No. 10/872,932, filed Jun. 21, 2004, entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976, 862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/ 16280, US96/18978, US91/09630, US91/05939, US94/ 01234, GB89/01334, GB91/01134, GB92/01755; WO90/ 14443, WO90/14424, WO90/14430, EP 229246, Colligan, Ausubel, Harlow and Lane, supra, each entirely incorporated herein by reference, included references cited therein.

The antibody can also be optionally generated by immunization of a transgenic animal (e.g., mouse, rat, hamster, non-human primate, and the like) capable of producing a repertoire of human antibodies, as described herein and/or as known in the art. Cells that produce a desired antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770, 428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591(1994), Green et al, Nature Genetics 7:13-21(1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7): 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

The method of the present invention thus provides a more efficient way of generating antibodies. Accordingly, the present invention also provides antibodies produced using the improved method of the present invention. The antibodies produced using the present invention can be used for therapeutic, diagnostic, and/or research purposes.

Having generally described the invention, the same will be more readily understood by reference to the following examples, which are provided by way of illustration and are not intended as limiting.

Example 1

Serum Starvation of FO Myeloma Cells Improves Hybridoma Fusion Efficiency

In order to determine whether the stage of the cell cycle of myeloma cells has any effect on hybridoma fusion efficiency, FO cells were synchronized for a period of time via serum deprivation (1% FBS). Afterwards, the synchronized FO cells were either directly fused to splenic B cells or allowed to recover for a period of time in complete media prior to the fusion. Briefly, five Balb/C mice were immunized with hen egg lysozyme in Titermax, boosted at 2 weeks, and harvested at 4 weeks. Spleens were obtained, single cell suspensions were pooled, run through a lympholyte M column, and counted. A naïve spleen was harvested separately and used as a negative control. FO myeloma cells were grown in DMEM+ 1% FBS for varying lengths of time, washed, and then recovered for indicated lengths of time in DMEM+10% FBS prior to fusion. Sixty×10^6 splenic cells were mixed with 60×10^6 FO cells for each sample (15×10^6 spenic and FO cells for the naïve control), fused with 50% PEG, and plated into 96-well plates in HAT medium at a density of 4×10^6 splenic cells per plate. Cell colonies were assessed 7-11 days post fusion. It was shown that serum deprivation without any recovery period did not increase fusion efficiency. On the other hand, serum deprivation followed with recovery led to an increase in fusion efficiency compared to FO cells incubated in complete media. It was determined that for FO myeloma cells, the optimal starvation time was 13 hours and the optimal recovery time was also 13 hours. Such treatment prior to fusion led to a 45% increase in fusion efficiency.

Myeloma cell samples obtained before treatment, immediately after 13 hours serum starvation, and after 13 hours recovery were stained with propidium iodide and analyzed on a flow cytometer for DNA content. Without treatment, 49-52% of cells were in G0/G1, 23-25% were in S phase, and 22% were in G2/M phase. Serum starvation did not significantly alter this ratio immediately after treatment, but significantly increased the population of cells in S phase to 38% following recovery. This is contrary to previous reports which suggested an increase in hybridoma fusion efficiency when cells were synchronized to the M phase. In summary, the present invention successfully increases the hybridoma fusion efficiency, which is highly efficient, and induces minimal or no adverse side effects.

It will be clear that the invention can be practiced otherwise than as particularly described in the foregoing description and examples. Numerous modifications and variations of the present invention are possible in light of the above teachings and, therefore, are within the scope of the present invention.

What is claimed is:

1. A method for increasing hybridoma fusion efficiency comprising synchronizing a cell selected from the group consisting of: i) a fusing partner myeloma cell; and ii) a fusing partner antibody producing B cell; wherein the synchronization is achieved by serum starvation followed by restoration of normal growth media.

2. The method of claim 1 wherein said myeloma cells are selected from the group consisting of P3-X63/Ag8, X63-Ag8.653, NS1/1.Ag 4 1, SP210-Ag14, FO, NSO/U, MPC-11, MPC11-X45-GTG 1.7 and S194/5XXO Bul.

3. The method of claim 1 wherein said antibody producing B-cell is obtained from a source selected from the group consisting of spleens, tonsils, lymph nodes, and peripheral blood.

* * * * *

UNITED STATES PATENT AND TRADEMARK OFFICE
CERTIFICATE OF CORRECTION

PATENT NO. : 8,216,842 B2
APPLICATION NO. : 12/443492
DATED : July 10, 2012
INVENTOR(S) : Jill Giles-Komar, Michael Rycyzyn and Gregory Bannish It is certified that error appears in the above-identified patent and that said Letters Patent is hereby corrected as shown below:

Column 8, line 11, delete "S194/5XXO" and insert --S194/5XX0--.

Signed and Sealed this
Twenty-fifth Day of December, 2012

David J. Kappos
*Director of the United States Patent and Trademark Office*